United States Patent [19]

Benz et al.

[11] Patent Number: 4,670,542

[45] Date of Patent: Jun. 2, 1987

[54] NEW ANTIBIOTICS, PREPARATION AND USE OF AND INTERMEDIATES THEREFOR

[75] Inventors: Günter Benz, Madison, Wis.; Karl G. Metzger, Wuppertal, Fed. Rep. of Germany; Jörg Pfitzner, Wuppertal, Fed. Rep. of Germany; Delf Schmidt, Wuppertal, Fed. Rep. of Germany; Hans-Joachim Zeiler, Velbert, Fed. Rep. of Germany

[73] Assignee: Bayer Aktiengesellschaft, Leverkusen, Fed. Rep. of Germany

[21] Appl. No.: 868,406

[22] Filed: May 29, 1986

Related U.S. Application Data

[62] Division of Ser. No. 669,176, Nov. 7, 1984.

[30] Foreign Application Priority Data

Nov. 17, 1983 [DE] Fed. Rep. of Germany ....... 3341571

[51] Int. Cl.[4] .............................................. C07K 5/08
[52] U.S. Cl. .................................................. 530/331
[58] Field of Search ........................................ 530/331

[56] References Cited

PUBLICATIONS

Chem. Abstr. vol. 104, (1986) 31433.
Chem. Abstr. vol. 101, (1984) 171741.
Chem. Abstr. vol. 104, (1986) 107903.

*Primary Examiner*—Delbert R. Phillips
*Attorney, Agent, or Firm*—Sprung Horn Kramer & Woods

[57] ABSTRACT

New antibiotics of the formula

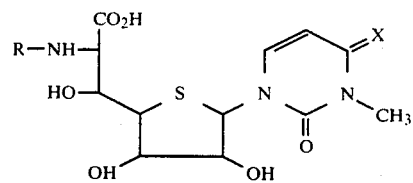

in which
X is O or N—CO—NH$_2$,
R is the radical of an aminoacid other than serine, an oligopeptide other than HyoHyoHyoSer or a derivative thereof on the free amino group, or a radical from the group comprising HyoSer, HyoHyoSer, HyoHyoHyoAla, HyoHyoHyoThr, Hyo, HyoHyo or HyoHyoHyo, and
Hyo is N$^5$-acetyl-N$^5$-hydroxy-L-ornithine.

The intermediate wherein R is H is also new as is the tripeptide

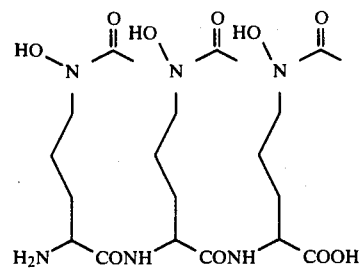

1 Claim, No Drawings

NEW ANTIBIOTICS, PREPARATION AND USE OF AND INTERMEDIATES THEREFOR

This is a divisional of application Ser. No. 669,176, filed Nov. 7, 1984, now pending.

The invention relates to new compounds of the general formula 1 in which

X represents O or N—CO—NH$_2$ and
R denotes the radical of an amino acid (with the exception of serine), an oligopeptide (with the exception of HyoHyoHyoSer and its derivatives on the free amino group) or a radical from the group comprising HyoSer, HyoHyoSer, HyoHyoHyoAla, HyoHyoHyoThr, Hyo, Hyo-Hyo or HyoHyoHyo, wherein Hyo denotes N$^5$-acetyl-N$^5$-hydroxy-L-ornithine.

An amino acid R is preferably a naturally occurring amino acid, in particular glycine, alanine, valine, leucine, isoleucine, phenylalanine, tyrosine, proline, hydroxyproline, threonine, cysteine, cystine, methionine, tryptophan, aspartic acid, asparagine, glutamic acid, glutamine, hydroxyglutamic acid, arginine, lysine or histidine, or an oligopeptide of these amino acids. Alanine and threonine are very particularly preferred.

The compounds according to the invention can be prepared as follows:

A compound of the formula 2 in which

X denotes O or N—CO—NH$_2$, is used as the starting compound. These compounds and their preparation are described in German Offenlegungsschriften (German Published Specification) Nos. 3,102,136 and 2,102,137 (corresponding to European Patent No. A-57,349 and 57,812 and U.S. Ser. Nos. 340,418 and 340,449). If a compound of the general formula (2) is split with a suitable enzyme, a compound of the general formula 3 in which

X=O or N—CO—NH$_2$, ps
is obtained—in addition to other products of splitting.

Peptide hydrolases of groups EC 3.4.11 (α-aminoacyl-peptide hydrolases) and EC 3.4.21-23 (proteases), in particular, are suitable for this purpose. α-Chymotrypsin, subtilisin, aminoacylase I, β-lactamase from E.coli T7, proteinase K and pronase K may be mentioned in particular.

When (2) are incubated with microsomal leucineaminopeptidase, the serine-free nucleosides (4) are obtained.

in which

X has the above-mentioned meaning.

The compounds (3) and (4) are useful intermediates for the preparation of the compounds of the general formula (1). Compound (4) is part of the invention.

The enzyme preferably used for the splitting of (2) to (4) is microsomal leucine aminopeptidase (manufacturer: Sigma; L 5006) with a specific activity of 10–20 U/mg (leucine amide as the substrate). (Here, U is the unit which hydrolyzes 1 μmol of L-leucine amide per minute to leucine and NH$_3$ at pH 8.5° and 25° C.).

The splitting is carried out in an aqueous medium at a pH value of 6.6 to 7.8, preferably at about 7.2. The reaction temperature is in general 20° to 40° C., preferably 37° C. The reaction time under the above-mentioned reaction conditions is not less than 2 days, preferably about 6 to 8 days.

If microsomal leucine aminopeptidase is used as the enzyme, $N^5$-acetyl-$N^5$-hydroxy-ornithine (5) and serine is also obtained—in addition to (4).

After the reaction, the particular compound according to the invention is separated from any other products of splitting which are present, that is to say is purified. Purification is carried out preferably by chromatography. It is preferably carried out on cellulose ion exchangers (for example Sephadex ®SP 25 H+, sodium chloride gradient as the eluant), adsorber resins and silica gel.

In the first process step, according to the invention, of the enzymatic splitting, it must be regarded as surprising that splitting to the nucleoside (4) takes place with the microsomal leucine aminopeptidase, since the nucleoside (4) is not a typical amino acid.

A new iron-complexing tripeptide [$N^5$-acetyl-$N^5$-hydroxy-L-ornithyl]-[$N^5$-acetyl-$N^5$-hydroxy-L-ornithyl]-$N^5$-acetyl-$N^5$-hydroxy-L-ornithine (7) can be obtained from the culture filtrate of a fermentation with Streptomyces spec. WS 116 (DSM 1692) after adsorption on Lewatit ® OC 1031, chromatography on its $Fe^{3\pm}$-charged cation exchanger, demineralization on Lewatit ® OC 1031 and chromatography on a strongly acid and subsequently on a weakly acid cation exchanger.

The same tripeptide (7) is found on enzymatic splitting of the compound (2) with endopeptidases to give the serine-containing nucleoside (3). Proteinase K and subtilisin are preferred here.

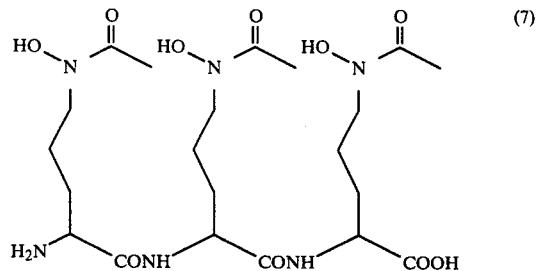

(7)

The intact tripeptide (HyoHyoHyo) (7) can be isolated as such from the reaction medium. It is in the form of a partial structure in part of the compound (1) and Likewise is part of the invention.

Starting from the serine nucleoside (3), the serine-free nucleoside (4) is in turn obtained only with the microsomal leucine aminopeptidase. Working up is effected as described above, preferably by chromatography.

The following measures are preferred in the further reaction of (3) and (4) to give (1).

The amino acids and peptides used are N-blocked. Preferred protective groups are the BOC (t-butoxycarbonyl) and the Z (benzyloxycarbonyl) group, which are inserted by customary processes of peptide chemistry in a basic medium. The hydroxyl function of the hydroxamic acid in derivatives of $N^5$-acetyl-$N^5$-hydroxy-ornithine (5) is benzyl-protected. The peptide linkage is effected by the mixed anhydride method. The protected amino acid and the peptide are activated in tetrahydrofuran at about $-20°$ C., preferably using isobutyl chloroformate/N-methylmorpholine. Coupling with the nucleosides (3) and (4) is then carried out in an aqueous organic medium, preferably in water/tetrahydrofuran mixtures. Alternatively, active esters (hydroxysuccinimide esters) of N-blocked amino acids or peptides can also be used in the coupling reaction. Deblocking is effected by hydrogenolysis over Pd (Z and benzyl protective group) or with trifluoroacetic acid/methylene chloride 1:1 (BOC protecting group).

The compounds of the formula (1) thus obtained are chromatographed on Sephadex[(2)] SP 25 H+ (development with a sodium chloride gradient) and demineralized on Lewatit ® OC 1031.

The following table shows particularly preferred compounds of the formula (1).

TABLE 1

| Compound | X = N—CO—NH$_2$ R = | Example | X = O R = |
|---|---|---|---|
| 8 | Ala | 21 | Ala |
| 9 | HyoHyoHyoAla | 22 | Hyo |
| 10 | His | 23 | HyoHyo |
| 11 | Hyo | 24 | HyoHyoHyo |
| 12 | HyoHyo | | |
| 13 | HyoHyoHyo | 25 | AlaSer |
| 14 | AlaSer | 26 | HisSer |
| 15 | HisSer | 27 | HyoSer |
| 16 | HyoSer | 28 | HyoHyoSer |
| 17 | HyoHyoSer | 29 | ThrSer |
| 18 | ThrSer | 30 | Thr |
| 19 | Thr | 31 | HyoHyoHyoThr |
| 20 | HyoHyoHyoThr | | |

The compounds (1) according to the invention have an antimicrobial activity which is demonstrated by the following in vitro experiments.

Activity against the germs listed below is found in vitro, on the basis of the diameter of the inhibiting areola.

TABLE 2

| | | Inhibiting areola diameter | | | | | | Medium DST agar | | | | | | | |
|---|---|---|---|---|---|---|---|---|---|---|---|---|---|---|---|
| | | E. coli T 7 (ug/ml) | | | E. coli 14 (ug/ml) | | | Klebs. 57 USA (ug/ml) | | | Prot. 1017 (ug/ml) | | | Staph. 133 (ug/ml) | | |
| Compound | Hole test | 1000 | 100 | 10 | 1000 | 100 | 10 | 1000 | 100 | 10 | 1000 | 100 | 10 | 1000 | 100 | 10 |
| 11 | X:N—CO—NH$_2$ R:Hyo | | 18+ | 13+ | | 13 | | | 18+ | | — | — | — | — | — | — |
| 13 | X:N—CO—NH$_2$ R:HyoHyoHyo | 19 | | | 20 | | | — | — | — | 20+ | | | — | — | — |
| 9 | X:N—CO—NH$_2$ R:HyoHyoHyo Ala | | 34+ | 28+ | | 34+ | 30 | | | | — | — | — | — | — | — |
| 20 | X:N—CO—NH$_2$ R:HyoHyoHyo | 15+ | 14+ | | 14+ | 13+ | | — | — | — | 17+ | | | 25+ | | |

TABLE 2-continued

| Com-pound | Hole test | Inhibiting areola diameter | | | | | | Medium DST agar | | | | | | | | |
|---|---|---|---|---|---|---|---|---|---|---|---|---|---|---|---|---|
| | | E. coli T 7 (ug/ml) | | | E. coli 14 (ug/ml) | | | Klebs. 57 USA (ug/ml) | | | Prot. 1017 (ug/ml) | | | Staph. 133 (ug/ml) | | |
| | | 1000 | 100 | 10 | 1000 | 100 | 10 | 1000 | 100 | 10 | 1000 | 100 | 10 | 1000 | 100 | 10 |
| 24 | Thr R:O R:HyoHyoHyo | | 18 | | | 18 | | — | — | — | | 18 | | — | — | — |

¹ Inhibiting areola with background growth

The compounds according to the invention can thus be used in combating bacterial diseases, in particular in the form of pharmaceutical compositions. Such pharmaceutical formulations consist of at least one of the active compounds according to the invention and, if appropriate, suitable non-toxic excipients and auxiliaries. Such pharmaceutical formulations likewise are part of the invention.

The present invention also includes pharmaceutical formulations in dosage units. This means that the formulations are in the form of individual parts, for example tablets, dragees, capsules, pills, suppositories and ampules of which the content of active compound corresponds to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, a half, a third or a quarter of a daily dose.

By non-toxic, pharmaceutically suitable excipients there are to be understood solid, semi-solid or liquid diluents, fillers and formulation auxiliaries of every kind.

Tablets, dragees, capsules, pills, granules, suppositories, solutions, suspensions and emulsions, pastes, ointments, gels, creams, lotions, powders and sprays may be mentioned as preferred pharmaceutical formulations.

Tablets, dragees, capsules, pills and granules can contain the active compound or compounds alongside the customary excipients, such as (a) fillers and extenders, for example starches, lactose, sucrose, glucose, mannitol and silica, (b) binders, for example carboxymethylcellulose. Alginates, gelatine and polyvinylpyrrolidone, (c) humectants, for example glycerol, (d) disintegrating agents, for example agar agar, calcium carbonate and sodium carbonate, (d) solution retarders, for example paraffin, and (f) absorption accelerators, for example quaternary ammonium compounds, (g) wetting agents, for example cetyl alcohol and glycerol monostearate, (h) adsorbents, for example kaolin and bentonite, and (i) lubricants, for example talc, calcium stearate and magnesium stearate and solid polyethylene glycols, or mixtures of the substances listed under (a) to (i).

The tablets, dragees, capsules, pills and granules can be provided with the customary coatings and shells, optionally containing opacifying agents, and can also be of such composition that they release the active compound or compounds only, or preferentially, in a certain part of the intestinal tract, optionally in a delayed manner, examples of embedding compositions which can be used being polymeric substances and waxes.

The active compound, optionally together with one or more of the above-mentioned excipients, can also be in a microencapsulated form.

Suppositories can contain, in addition to the active compound, the customary water-soluble or water-insoluble excipients, for example polyethylene glycols, fats, for example cacao fat, and higher esters (for example $C_{14}$-alcohol with $C_{16}$-fatty acid), or mixtures of these substances.

Ointments, pastes, creams and gels can contain, in addition to the active compound, the customary excipients, for example animal and vegetable fats, waxes, paraffins, starch, tragacanth, cellulose derivatives, polyethylene glycol, silicones, bentonites, silica, talc and zinc oxide, or mixtures of these substances powders and sprays can contain, in addition to the active compound, the customary excipients, for example lactose, talc, silica, aluminum hydroxide, calcium silicate and polyamide powder, or mixtures of these substances. Sprays can additionally contain the customary propellants, for example chlorofluorohydrocarbons.

Solutions and emulsions can contain, in addition to the active compound, the customary excipients, such as solvents, solubilizing agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cottonseed oil, groundnut oil, corn germ oil, olive oil, castor oil and sesame oil, glycerol, glycerol formal, tetrahydrofuryl alcohol, polyethylene glycols and fatty acid esters of sorbitan, or mixtures of these substances.

For parenteral administration, the solutions and emulsions can also be in a sterile form which is isotonic with blood.

Suspensions can contain, in addition to the active compound, the customary excipients, such as liquid diluents, for example water, ethyl alcohol and propylene glycol, suspending agents, for example ethoxylated isostearyl alcohols, polyoxyethylene sorbitol and sorbitan esters, microcrystalline cellulose, aluminum metahydroxide, bentonite, agar-agar and tragacanth, or mixtures of these substances.

The formulation forms mentioned can also contain colorants, preservatives and additives which improve the odor and flavor for example peppermint oil and eucalyptus oil, and sweeteners, for example saccharin.

The compounds according to the invention should preferably be present in the above-mentioned pharmaceutical formulations in a concentration of about 0.1 to 99.5, preferably about 0.5 to 95, percent by weight of the total mixture.

The above-mentioned pharmaceutical formulations can also contain other pharmaceutically active compounds, in addition to the active compound according to the invention.

The above-mentioned pharmaceutical formulations can be prepared in the customary manner by known methods, for example by mixing the active compound with the excipient or excipients.

The present invention also relates to the use of the active compounds according to the invention and of pharmaceutical formulations which contain the active compound according to the invention, in human and veterinary medicine, for the prevention, alleviation and/or cure of diseases.

The active compound or the pharmaceutical formulations can be administered locally, orally, parenterally, intraperitoneally and/or rectally, preferably orally and parenterally, in particular intramuscularly or intravenously, if appropriate also as a continuous intravenous drip.

In general, it is advisable, in the case of oral or parenteral administration, to administer the active compounds according to the invention in total amounts of about 10 to 1,000, preferably 50 to 600, mg/kg of body weight every 24 hours, if appropriate in the form of several individual administrations, in order to achieve the desired results. An individual administration preferably contains the active compounds according to the invention in amounts of about 50 to about 300 mg/kg of body weight, in particular 100 to 200 mg/kg of body weight.

However, it may be necessary to deviate from the dosages mentioned, and in particular to do so as a function of the nature and severity of the disease, the nature of the formulation and of the administration of the medicament and the time or interval over which administration takes place. Thus it can in some cases suffice to manage with less than the above-mentioned amount of active compound, whilst in other cases the above-mentioned amount of active compound must be exceeded. The particular optimum dosage required and the type of administration of the active compound can easily be determined by anyone skilled in the art on the basis of his expert knowledge.

EXAMPLE 1

Fermentation batch

The microorganism strain Streptomyces spec. WS 116 (DSM 1692) known from DE-OS (German Published Specification) No. 3,102,137 was cultured in precultures in a nutrient solution composed of 2% by weight of glucose, 1.3% of yeast extract, 0.05% of polyol and tapwater. The pH was brought to 6.5 before the sterilization. 4×1,000 ml conical flasks each containing 150 ml of this nutrient solution were inoculated with the strain and were incubated for 4 days at 28° C. on a rotary shaking machine at 220 revolutions/minute. A second preculture in a laboratory fermenter containing 20 liters of nutrient solution was inoculated with these precultures and was incubated at 200 revolutions/minute with 10 liters of air/minute at 28° C. for 3 days. A production fermenter containing 600 liters of nutrient solution having the following composition was inoculated with this culture: 0.7% by weight of citric acid, 0.4% by weight of L-arginine, biochemical grade, 0.15% by weight of $Na_2SO_4$, 0.1% by weight of $MgSO_4.7H_2O$, 0.1% by weight of $K_2HPO_4$, 0.05% by weight of $CaCO_3$, 0.01% by weight of $MnCl_2.4 H_2O$, 0.01% by weight of $CoCl_2.6 H_2O$, 0.01% by weight of $ZnCl_2$, 0.01% by weight of $FeCl_3.6 H_2O$ and 0.05% by weight of polyol (anti-foaming agent) and tapwater.

The pH value of this nutrient solution was brought to 6.2 with NaOH before the sterilization.

The production culture was incubated at 26° C. with a stirring speed of 100 revolutions/minute and an aeration of 80 liters of air/minute.

After about 3 days, a pH value of 8.5 to 8.8 was reached. From this time on a constant pH value of 7.5 was maintained, under otherwise unchanged conditions, by feeding in a feeding concentrate. The feeding concentrate consisted of 40% by weight of citric acid, 4% by weight of L-arginine and the abovementioned mineral salts in the abovementioned concentrations in tapwater. (All the nutrient solutions were sterilized at 121° C. for 30 minutes).

During the fed-batch fermentation, compound (2) (X=N—CO—$NH_2$) was initially formed. In a later phase—about—after 10 days, the new tripeptide (7) was formed. The end point of the fermentation was determined with the aid of analytical tests.

EXAMPLE 2

Isolation of [$N^5$-acetyl-$N^5$-hydroxy-L-ornithyl]-[$N^5$-acetyl-$N^5$-hydroxy-L-ornithyl]-$N^5$-acetyl-$N^5$-hydroxy-L-ornithine (7).

4,000 liters of culture broth (pH 9.06) containing compound (2) and tripeptide (7) were brought to pH 6.2 with 50 liters of 1:1 dilute hydrochloric acid. 400 g of $FeCl_3.6 H_2O$ were added, the mixture was stirred and 25 liters of dilute NaOH were then added with stirring, to bring the pH to 7. Separation was then carried out at 200 to 250 liters/hour in a Westfalia separator. The supernatant liquor was passed through a 30×70 cm high column filled with Lewatit OC 1031 (a non-specific adsorption resin from BAYER AG). The column was washed successively with 1,000 liters of deionized water and 1,000 liters of 15% strength methanol. The iron-complexing substances (siderochromes) were eluted from the column with 50% strength methanol and collected in 100 liter fractions. Fractions containing tripeptide were combined, concentrated to about 20 liters in a thin film evaporator and then freeze-dried. 342 g of crude product were obtained and were then dissolved in 6 liters of water, and 25 ml of 50% strength $FeCl_3$ solution were added, with stirring. The precipitate which formed was centrifuged off after stirring for 15 minutes (Hettich Rota Magna centrifuge, 1.5 liter beaker, 30 minutes, 4,000 rpm). The supernatant liquor was passed under gravity over an 8×45 cm high column filled with SP-Sephadex C 25 $Fe^{+++}$. The flow rate was 4 liters per hour. The black-colored column was rinsed with 5 liters of distilled $H_2O$, followed by 10 liters of 0.2M $NaH_2PO_4$/0.3 NaCl buffer. The column, which was now still colored only light brown, was now eluted with 0.2M $NaH_2PO_4$/0.3M NaCl/0.05M EDTA (flow rate 2-3 liters hour) and the column eluate was collected fractionally in 500 ml portions. Fractions 6-14, which contained iron-complexing substances, were combined and passed over a 5×40 column filled with Lewatet OC 1031. The flow rate was 2 liters/hour. The column was then washed with distilled water until no chloride ions were to be detected with $AgNO_3$ in the column eluate (about 6 liters, flow rate 5 liters/hour). The column was subsequently eluted with 3 liters of 90% strength methanol which were collected as a batch, concentrated and lyophilized.

Yield: 6.74 g.

The product thus obtained was discharged, as a solution in 100 ml of $H_2O$, onto a 2.5×30 cm high column filled with Sephadex® SP 25 $H^+$. The column was rinsed with 1 liter of distilled $H_2O$ and then developed with 4 liters of a linear gradient (0 to 0.1M NaCl). The column eluate was neutralized immediately by metering in 0.5M Sörensen buffer, pH 6.5, and was fractionated into portions of 20 ml. Aliquots of the fractions were tested for iron complex formation with 0.1M $FeCl_3$ (red coloration). Two iron-complexing fractions were obtained and were combined. Each of these fractions was demineralized, as described, in each case over a Lewatit OC 1031 column (2.5×30 cm). Fraction I of 620 mg and fraction II=2.3 g were obtained.

Fraction I was dissolved in 5 ml of $H_2O$ and introduced onto a 0.9×100 cm column filled with carboxymethylcellulose (Wathmann, CM 52 grade) in the $H^+$ form. The column was developed with distilled water. Three compounds which complex with iron were obtained in the eluate, and were lyophilized separately. The compound finally eluted contained the tripeptide (7) and gave 120 mg of lyophilizate.

$^1$H-NMR ($D_2O$, 250 MHz): δ=1.54–1.96 (m; 12H, β, γ-$CH_2$—); 2.12 (s; 9H, N—CO—$CH_3$); 3.64 (mc; 6H, δ—$CH_2$—), 4.04 (t, J=7 Hz; 1H, NH—CH—); 4.14 (mc; 1H, NH—CH—); and 4.40 (mc; 1H, NH—CH—).

$^{13}$C-NMR ($D_2O$, 62, 83 MHz): ppm=18.8(3)q; 20.9 t; 21.8 t; 22.1 t; 27.5(2)t; 28.3 t; 46.6 t; 46.7 t; 47.1 t; 52.1 d; 53.1 d; 54.5 d; 168.9 s; 171.7 s; 173.5(3)s; and 177.6 s.

$[α]_D^{20}$ −8.57 (c=0.567, 1N HCL). FAB-MS: m/z=535 (; M+H); $C_{21}H_{39}N_6O_{10}$.

$C_{21}H_{38}N_6O_{10} \times H_2O$ (552.59)

calculated: C, 45.7; H, 7.3; N, 15.2; found: C, 45.7; H, 7.3; N, 15.0.

EXAMPLE 3

Production of the tripeptide (7) by enzymatic splitting of compound (2) (X=N—CO—$NH_2$)

10 g of compound (2) (X=N—CO—$NH_2$) were dissolved in 100 ml (100 mg/ml) of 0.1M ammonium carbonate buffer, pH 7.5, and the pH value was corrected to 7.5.

100 mg of proteinase K (prot. K from fungi, 20 mA units/mg; Merck; Order No.: 140 799) were added to the solution. The mixture was incubated overnight at 37° C. The hydrolyzate was then gently concentrated to dryness 3 times in a rotary evaporator, redissolved in a little distilled $H_2O$, introduced into a dialyzing tube and dialyzed against 2×1 liter of distilled $H_2O$ at 4° C. for 2×12 hours (in each case 100 ml of distilled $H_2O$ per 1 g of starting substance). The dialyzates were combined and concentrated and the residue was lyophilized.

A solution of 3 g of the above lyophilizate in 25 ml of distilled $H_2O$ was discharged onto a well-packed 0.5 cm×100 cm Pharmacia column filled with Biogel P-2 (200∝400 mesh; Bio-Rad) with a flow rate of 200 ml/hour. The column was eluted with distilled $H_2O$ with a flow rate of 200 ml/hour. 200 glasses with 8 minute fractions=about 25 ml were collected.

10–20 μl of the fraction were applied to Opti UPC12 (Fluka) plates and developed in a citrate/acetonitrile eluant. (Eluant: dilute citrate buffer Merck Titrisol pH 4 to 150 ml with distilled water, add 20 ml of 0.1M $FeCl_3$ and make up to 200 ml with acetonitrile.)

Migration zone: 10 cm

Staining: iron-3 chloride)

50–100 μg of tripeptide (7) were also applied for comparison.

The tripeptide-containing fractions were combined and concentrated and the concentrate was lyophilized. Yield: 500–700 mg of tripeptide (7).

Besides having identical $^1$H—and $^3$C-NMR spectroscopic data (see Example 2), the tripeptide (7) thus obtained had an optical rotation $[α]_{20}^D$ of −8.63 (c=1.008, 1N HCl).

EXAMPLE 4

Nucleoside (4), X=N—CO—$NH_2$, from compound (2), X=N—CO—$NH_2$

In two parallel batches, in each case 1.5 g (1.5 mmol) of compound (2) (X=N—CO—$NH_2$) were dissolved in 500 ml of bidistilled $H_2O$ and the pH was brought to 7.2 with 0.5M tris buffer. In each case 0.75 ml (46.9 units) of leucine aminopeptidase (microsomal), manufacturer: Sigma L 5006; specific activity 10–20 units/mg, 37° C., leucine amide as the substrate) were added to the solution and the mixtures were stirred at 37° C. Leucine aminopeptidase was added to the batches after 16 hours (28.1 units, 5 days (12.5 units) and 6 days (12.5 units). The reaction had ended after 7 days. The batches were combined and freeze-dried. The lyophilizate was chromatographed on 300 ml of Sephadex SP 25 in a low-temperature laboratory (4° C.) (first runnings of 700 ml of bidistilled water, followed by a gradient of 0.01–0.5N NaCl solution, flow rate 5 ml/minute, size of fraction=20 ml). 0.5M Sörensen buffer was pumped into the runnings so that the collected fractions had a pH of 6.7. The identical fractions were collected, after high pressure liquid chromatography and analysis by thin layer chromatography, and were demineralized on Lewatit LGP 4067.

Fractions 131–140: 41.8 mg

Fractions 164–244: 626.8 mg, 53.7%

Fractions 228–235: 126.4 mg $^1$H-NMR ($D_2O$, 250 MHz): δ=3.39 (s; 3H, N—$CH_3$); 3.98 (d, J=3.8 Hz; 1H, H-6'); 4.07 (dd, J=6.5 Hz; J=4.8 Hz; 1H, H-4'); 4.36–4.48 (m, 2H, H-2', 3'); 4.55 (dd, J=6.5 Hz, J=3.8 Hz, 1H, H-5'); 5.92 (d, J=4.0 Hz; 1H, H-1'); 6.48 (d, J=8.0 Hz; 1H, H-5); and 8.36 (d, J=8.0 Hz; 1H, H-6).

$^{13}$C-NMR ($D_2O$, dioxane as the standard, 50.32 MHz): ppm=170.4 (s; C-7'); 166.8 (s; N—CO—$NH_2$); 155.1 (s, pyrimidine C-4); 151.9 (s, pyrimidine C-2); 137.0 (d, pyrimidine C-6); 96.0 (d, pyrimidine C-5); 80.0 (d); 74.5 (d); 67.3 (d); 65.3 (d); 57.3 (d, C-6'); 54.1 (d, C-4'); and 29.3 (qu, N'$CH_3$).

UV (1N HCl): $λ_{max}$=214 (10490), 235 (8205) and 305 (15306).

$[α]_D^{20}$=33.61±0.08 (c=1.02; $H_2O$). FAB-MS: m/z=390 (6.7%, M+H).

$C_{13}H_{19}N_5O_7S \times H_2O$ (molecular weight 407.40) calculated: C, 38.2; H, 5.2; N, 17.2; O, 31.4; S, 7.9; found: C, 38.2; H, 5.1; N, 16.8; O, 31.7.

EXAMPLE 5

Nucleoside (4) from compound (3), X=N—CO—$NH_2$ 10 g of compound (2) were dissolved in 100 ml of 0.1M ammonium carbonate buffer, pH 7.5. (Concentration 100 mg/ml) The pH value was corrected to 7.5. 1,500 units/mg of pig kidney leucine aminopeptidase were added to the solution. The mixture was incubated in an incubation cabinet at 37° C. for 3 days. The incubate was then evaporated to dryness in a rotary evaporator 3 times, redissolved in a little distilled $H_2O$ and introduced into a dialyzing tube. Dialysis was carried out twice overnight in a low-temperature laboratory against distilled $H_2O$ with 20 times the starting volume. The dialyzate was concentrated in a rotary evaporator and the concentrate was lyophilized.

Yield: 9–10 g of crude material containing 70 to 90% of nucleoside (4), X=N—CO—$NH_2$, were obtained.

For purification, in each case 3 g of the crude serine-free nucleoside (4) were discharged onto a 5×90 cm column filled with Biogel P 2 in distilled H$_2$O. The column was developed with distilled H$_2$O and the nucleoside-containing fractions were combined. After concentration, the concentrate was lyophilized. Yield: 1.8–2 g of the serine-free nucleoside (4).

All the spectroscopic data agreed with those from Example 4.

EXAMPLE 6

Nucleoside (4), X=O, R=H 1.5 g (1.6 mmol) of compound 2 (X=O) were dissolved in 500 ml of bidistilled water and the pH was brought to 7.2 with 0.5M tris buffer. 0.75 ml (46.9 units) of leucine aminopeptidase (microsomal, manufacturer: Sigma L. 5006; specific activity 10–24 units/mg; 37° C., Leucine amide as the substrate) was added to the solution and the mixture was stirred at 37° C. Leucine aminopeptidase was added to the batch after 16 hours (25 units), 2 days (25 units) and 3 days (25 units). The reaction had ended after 7 days. The solution was freeze-dried and demineralized on 300 ml of lewatit LGP 4067 (6). Washing was carried out with bidistilled water until the UV-active material had been eluted. The residual product was eluted with methanol:water 1:1.

Fractions 11–29: 1.7 g, salt and hydroxamic acid (5)
Fractions 30–47: 544 mg, (4) (99.4%)
Melting point: 105°–10° C. (decomposition)

$^1$H-NMR (D$_2$O, 250 MHz): δ=3.29 (s; 3H, N—CH$_3$); 3.94 (d, J=4 Hz; 1Hz; 1H, Hz; 1H, H-6′); 4.04 (dd, J=6 Hz; 1H, H-4′); 4.36–4.50 (m; 2H, H-2′, 3′); 4.56 (dd, J=6 Hz, J=4 Hz; 1H, H-5′); 5.94 (d, J=6 Hz; 1H, H-1′); 5.96 (d, J=8 Hz; 1H, H-5); and 8.45 (d, J=8 Hz; 1H, H-6).

$^{13}$C-NMR (D$_2$O, dioxane as the standard, 50.32 MHz): ppm=170.0 (s; C-7′); 164.9 (s, pyrimidine C-4); 152.2 (s, pyrimidine C-2); 141.5 (d, pyrimidine C-6); 100.1 (d, pyrimidine C-5); 80.4 (d); 74.7 (d); 67.6 (d); about 65 (d) (overlapping of dioxane); 56.9 (d, C-6′); 52.0 (d, C-4′); and 27.4-(qu, N—CH$_3$).

UV (1N HCl): λ$_{max}$=210 (8383); 266 (7097).

[α]$_D^{20}$+3.69±0.08 (c=0.994; H$_2$O).

FAB-MS: m/z=348 (3.3%; M+H).

C$_{12}$H$_{17}$N$_3$O$_7$S×H$_2$O (molecular weight 365.36) calculated: C, 39.4; H, 5.2; N, 11.5; O, 35.0; S, 8.8; found: C, 38.6; H, 5.2; N, 11.5; O, 36.0.

EXAMPLE 7

Hydroxamic acid (5)

4.9 g of a mixture of salt and hydroxamic acid (5) from the preparation of (4), X=O, were chromatographed on 200 ml of QAE Sephadex A 25 (OH form). After washing with 1.1 liters of bidistilled water, elution was carried out with 0.1N HCl. The fractions stained with iron-III chloride (uniform according to thin layer chromatography) were combined and crystallized from ethanol/water. 1.25 g of crystalline hydroxamic acid (5) were obtained.

Melting point: 221° C. (decomposition).

[α]$_D^{20}$=+3.37 (c=1.005; 1=1, H$_2$O).

$^1$H-NMR (D$_2$O, 250 MHz): δ=1.63–1.92 (m; 4H, —CH$_2$—CH$_2$—); 2.12 (s; 3H, N—COCH$_3$); 3.65 (mc; 2H, N—CH$_2$—); and 3.74 (mc; 1H, N—CH). MS (70 ev): m/z=190 (3%, M+), 145 (5%), 86 (19%), 43 (100%).

C$_7$H$_{14}$N$_2$O$_4$ (190.2) calculated: C, 44.2; H, 7.4; N, 14.7; found: C, 44.1; H, 7.4; N, 14.7

EXAMPLE 8

Alanyl-nucleoside (8)

100 mg (0.26 mmol) of serine-free nucleoside (4), X=N—CO—NH$_2$, and 21.8 mg (0.26 mmol) of sodium bicarbonate were dissolved in 10 ml of water/tetrahydrofuran 1:1. After addition of 147.1 mg (0.51 mmol) of BOC-L-alanine-hydroxysuccinimide ester, the mixture was stirred at 25° C. for 16 hours. A further 21.8 mg (0.26 mmol) of sodium bicarbonate and 73.6 mg (0.26 mmol) of the activated aminoacid were then added. After a further 16 hours, the solution was concentrated and the residue was dried under a high vacuum. The residue was taken up in a little water and the pH was brought to 7 with 2N sodium hydroxide solution. The mixture was chromatographed on 40 ml of Sephadex 25 H+ (column diameter: 1.5 cm; eluting agent: continuous gradient of 500 ml H$_2$O→0.1N NaCl). The fractions containing the substance were freeze-dried and then demineralized on 30 ml of Lewatit ® LGP 4067. After freeze-drying, 54.7 mg (46.3%) of the alanyl-nucleoside (8) were obtained. For the physical data, see Table 3.

EXAMPLE 9

Peptidyl-nucleoside (9)

57 mg (0.55 mmol) of [N$^5$-acetyl-N$^5$-O-benzyl-N$^2$-carboxybenzyl-L-ornithyl]-[N$^5$-acetyl-N$^5$-O-benzyl-L-ornithyl]-N$^5$-acetyl-N$^5$-O-benzyl-L-ornithine (derivative of trihydroxamic acid (2)) were dissolved in 5 ml of anhydrous tetrahydrofuran and the solution was cooled to −20° C. After addition of 0.061 ml (0.55 mmol) of N-methylmorpholine, 0.068 ml (0.55 mmol) of isobutyl chloroformate in 1 ml of anhydrous tetrahydrofuran was added. After activation at −20° C. for 30 minutes, 100 mg (0.22 mmol) of alanyl-nucleoside (8) in 5 ml of tetrahydrofuran/H$_2$O 1:1 were rapidly added dropwise and the mixture was stirred for 16 hours, while thawing to 25° C. The solution was concentrated, the concentrate was taken up in water and the pH was brought to 2 with 1N HCl. After several extractions with ethyl acetate/tetrahydrofuran 1:1 (60 ml in total), and after drying and evaporating on a rotary evaporator, 510 mg of crude substance were obtained (N, O blocked). This crude material was dissolved in 50 ml of ethanol/water 6:4 (parts by volume) and hydrogenated over 100 ml of palladium/charcoal with the aid of a vibromixer (25° C., normal pressure). After 3 hours, 100 mg of palladium-on-charcoal were added, and after 6 hours 50 mg of palladium-on-charcoal were added. After 9 hours, the deblocking had ended. The catalyst was filtered off hot and rinsed several times with ethanol/water 1:1. The filtrate was partly concentrated and then freeze-dried. 310 mg of the deblocked crude material were chromatographed on 30 ml of Sephadex SP 25H+ (column diameter: 1.5 cm; eluting agent: 100 ml of water; continuous gradient of 800 ml H$_2$O→0.1N NaCl; flow rate 2.5 ml/minute; fraction size 10 ml). After demineralization of the uniform fractions on Lewatit ® LGP 4067, 11.5 mg of the peptidyl-nucleoside (9) were obtained. For the physical data, see Table 3.

Compounds 10 to 33 were prepared analogously to Examples 5 and 6.

For the physical data, see Table 3.

TABLE 3

| | X: N—CO—NH$_2$ R: | $^1$H—NMR (D$_2$O, 250 MHz, HDO as an internal standard 4.80 ppm) δ [ppm]; J = line intervals (Hz) | UV (qualitative, 0.1 n HCl) λ$_{max}$ (nm) | Empirical formula | FAB-MS (Fast Atom Bombardment) |
|---|---|---|---|---|---|
| 8 | Ala | 1.56 (d, J=7.5 Hz; 3H, —CH—CH$_3$); 4.13 (qu, J=7.5 Hz; 1H, N—CH—). | 304 | C$_{16}$H$_{24}$N$_6$O$_8$S | |
| 9 | HyoHyoHyoAla | 1.39 (d, J=7.1 Hz; 3H, —CH—CH$_3$); 1.56-1.98 (m; 12H, —CH$_2$—); 2.13 (s; 9H, N—CO—CH$_3$); 3.67 (mc; 6H, N—CH$_2$—). | 305 | C$_{37}$H$_{60}$N$_{12}$O$_{17}$S | M-H 975 (1%) |
| 10 | His | 3.17-3.43 (m; 3H, N—CH—CH$_2$—C=); 7.40 (s; 1H, N—CH=C); 8.59 (s; 1H, N—CH=N—). | 305 | C$_{19}$H$_{26}$N$_8$O$_8$S | |
| 11 | Hyo | 1.62-2.04 (m; 4H, —CH$_2$—); 2.14 (s; 3H, N—CO—CH$_3$); 3.67 (mc; 2H, N—CH$_2$—); 4.09 (t, J=6 Hz; 1H, N—CH—). | 304 | C$_{20}$H$_{21}$N$_7$O$_{10}$S | |
| 12 | HyoHyo | 1.69-2.07 (m; 8H, —CH$_2$—); 2.22 (s; 6H, N—CO—CH$_3$); 3.73 (mc; 4H, N—CH$_2$—); 4.14 (t, J=6 Hz; 1H, N—CH—). | 306 | C$_{27}$H$_{43}$N$_9$O$_{13}$S | |
| 13 | HyoHyoHyo | 1.61-1.97 (m; 12H, —CH$_2$—); 2.15 (s, 9H, N—CO—CH$_3$); 3.67 (mc; 6H, N—CH$_2$—); 4.08 (t, J=6 Hz; 1H, N—CH—). | 306 | C$_{34}$H$_{55}$N$_{11}$O$_{16}$S | M-H 904 (1%) |
| 14 | AlaSer | 1.56 (d, J=7.5 Hz; —CH—CH$_3$); 4.14 (qu, J=7.5 Hz; 1H, N—CH—). | 305 | C$_{19}$H$_{29}$N$_7$O$_{10}$S | |
| 15 | HisSer | 3.43 (mc; 2H, —CH$_2$—C=); 7.41 (s; 1H, N—CH=C); 8.63 (s; 1H; N—CH=N). | 305 | C$_{22}$H$_{31}$N$_9$O$_{10}$S | |
| 16 | HyoSer | 1.71-2.07 (m; 4H, —CH$_2$—); 2.20 (s; 3H, N—CO—CH$_3$); 3.72 (mc; 2H, N—CH$_2$—); 4.17 (t, J=6.2 Hz; 1H, N—CH—). | 304 | C$_{23}$H$_{36}$N$_8$O$_{12}$S | |
| 17 | HyoHyoSer | 1.65-1.97 (m; 8H, —CH$_2$—); 2.15 (s, 6H, N—CO—CH$_3$); 3.68 (mc; 4H, N—CH$_2$—); 4.08 (t, J=6 Hz; 1H, N—CH—). | 306 | C$_{30}$H$_{48}$N$_{10}$O$_{15}$S | |
| 18 | ThrSer | 1.31 (d, J=6 Hz; 3H, CH—CH$_3$); 3.95 (d, J=6 Hz; 1H, N—CH—); 4.12 (qui, J=6 Hz; 1H, —O—CH—). | 305 | C$_{20}$H$_{31}$N$_7$O$_{10}$S | |
| 19 | Thr | 1.31 (d, J=6 Hz; 3H, CH—CH$_3$); 3.94 (d, J=6 Hz; 1H, N—CH—); 4.19 (qui, J=6 Hz; 1H, —O—CH—). | 304 | C$_{17}$H$_{26}$N$_6$O$_9$S | |
| 20 | HyoHyoHyoThr | 1.21 (d, J=6 Hz; 3H, CH—CH$_3$); 1.45-1.99 (m; 12H, —CH$_2$—); 2.15 (s; 9H, N—CO—CH$_3$); 3.68 (mc; 6H, —CH$_2$—); 4.08 (t, J=5 Hz; 1H, N—CH—); 4.28 (qu, d, J=6 Hz; 1H, N—CH—). | 306 | C$_{38}$H$_{62}$N$_{12}$O$_{18}$S | M-H 1005 (1.5%) |
| 21 | Ala | 1.63 (d, J=6 Hz; 3H, CH—CH$_3$); 4.21 (qu; J=6 Hz; 1H, N—CH—). | 265 | C$_{15}$H$_{22}$N$_4$O$_8$S | |
| 22 | Hyo | 1.62-2.00 (m; 4H, —CH$_2$—); 2.12 (s; 3H, N—CO—CH$_3$); 3.65 (mc; 2H, N—CH$_2$—); 4.07 (t, J=6 Hz; 1H, N—CH—). | 265 | C$_{19}$H$_{29}$N$_5$O$_{10}$S | |
| 23 | HyoHyo | 1.62-2.00 (m; 8H, —CH$_2$—); 2.16 (s; 6H, N—CO—CH$_3$); 3.68 (mc; 4H, N—CH$_2$—); 4.09 (t, J=6 Hz; 1H, N—CH—). | 263 | C$_{26}$H$_{41}$N$_7$O$_{13}$S | |
| 24 | HyoHyoHyo | 1.56-1.96 (m; 12H, —CH$_2$—); 2.14 (s; 9H, N—CO—CH$_3$); 3.67 (mc; 6H, N—CH$_2$—); 4.07 (t, J=6 Hz; 1H, N—CH—). | 264 | C$_{33}$H$_{53}$N$_9$O$_{16}$S | M-H 862 (1%) |
| 25 | AlaSer | 1.65 (d, J=7.5 Hz; 3H, CH—CH$_3$); 4.23 (qu, J=7.5 Hz; 1H, N—CH—). | 265 | C$_{18}$H$_{27}$N$_5$O$_{10}$S | |
| 26 | HisSer | 3.36 (dd, J=15 Hz; J=7.5 Hz; 1H, N—CH—CH$_2$); 3.46 (dd, J=15 Hz; J=5 Hz; 1H, —N—CH—CH$_2$—); 3.76-3.90 (m; 1H, N—CH); 7.38 (s; 1H, N—CH=C—); 8.62 (s; 1H, N—CH=N—). | 266 | C$_{21}$J$_{29}$H$_7$O$_{10}$S | |
| 27 | HyoSer | 1.67-2.03 (m; 4H, —CH$_2$—); 2.15 (s; 3H, N—CO—CH$_3$); 3.62-3.76 (m; 2H, N—CH$_2$—); 4.13 (t, J=6 Hz; 1H, N—CH—). | 265 | C$_{22}$H$_{34}$N$_6$O$_{12}$S | |
| 28 | HyoHyoSer | 1.65-2.09 (m; 8H, —CH$_2$—); 2.19 (s; 6H, N—CO—CH$_3$); 3.71 (mc; 4H, N—CH$_2$—); 4.11 (t, J=6 Hz; 1H, N—CH—). | 265 | C$_{29}$H$_{46}$N$_8$O$_{15}$S | |
| 29 | ThrSer | 1.35 (d, J=7 Hz; 3H, —CH—CH$_3$); 4.01 (d, J=5.8 Hz; 1H, N—CH—). | 264 | C$_{19}$H$_{29}$N$_5$O$_{11}$S | |
| 30 | Thr | 1.37 (d, J=6 Hz; 3H, —CH—CH$_3$); 3.97 (d, J=6.9 Hz; 1H, N—CH—); 4.24 (qui, J=6 Hz; 1H, —O—CH). | 264 | C$_{16}$H$_{24}$N$_4$O$_9$S | |
| 31 | HyoHyoHyoThr | 1.19 (d, J=6 Hz; 3H, —CH—CH$_3$); 1.55-1.97 (m; 12H, —CH$_2$—); 2.15 (s; 9H, N—CO—CH$_3$); 3.66 (mc; 6H, N—CH$_2$); 4.06 (t, J=6 Hz; 1H, N—CH—); 4.27 (qu, d. J=6 Hz; J=5 Hz; 1H, O—CH—CH$_3$). | 266 | C$_{37}$H$_{60}$N$_{10}$O$_{18}$S | |

It is understood that the specification and examples are illustrative but not limitative of the present invention and that other embodiments within the spirit and scope of the invention will suggest themselves to those skilled in the art.

We claim:
1. A compound of the formula
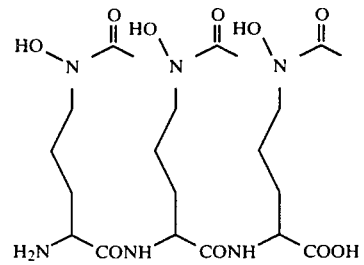

UNITED STATES PATENT AND TRADEMARK OFFICE
CERTIFICATE OF CORRECTION

PATENT NO. : 4,670,542

DATED : June 2, 1987

INVENTOR(S) : Günter Benz, et al.

It is certified that error appears in the above-identified patent and that said Letters Patent is hereby corrected as shown below:

| | |
|---|---|
| Col. 2, line 14 | After "$NH_2$," delete "ps" |
| Col. 3, line 9; Col. 4, line 19; Col. 12, lines 20 and 59 | Delete "$H^+$" and substitute --$H^{\oplus}$-- |
| Col. 4, line 19 | After "Sephadex" delete "$^{(2)}$" and substitute --®-- |
| Col. 9, line 21 | Delete "HCL" and substitute --HCl-- |
| Col. 9, line 48 | After "200" delete "∝" and substitute -- - -- |
| Col. 10, line 42 | Delete "N'$CH_3$" and substitute --N-$CH_3$-- |
| Col. 11, line 18 | Delete "10-24" and substitute --10-20-- |
| Col. 11, line 32 | After "(d,J=4 Hz;" delete "1 Hz; 1H, Hz'" |
| Col. 13, No. 30 | End of 2nd column, after "$CH_3$)" delete "." and substitute --;-- |

Signed and Sealed this

Nineteenth Day of April, 1988

Attest:

DONALD J. QUIGG

Attesting Officer

Commissioner of Patents and Trademarks